US007396940B2

(12) United States Patent
Cai et al.

(10) Patent No.: US 7,396,940 B2
(45) Date of Patent: Jul. 8, 2008

(54) COMBINATORIAL LIBRARY OF 3-ARYL-1H-INDOLE-2-CARBOXYLIC ACID

(75) Inventors: Jianping Cai, West Caldwell, NJ (US); Robert Alan Goodnow, Jr., Gillette, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 387 days.

(21) Appl. No.: 10/957,159

(22) Filed: Oct. 1, 2004

(65) Prior Publication Data

US 2005/0089935 A1    Apr. 28, 2005

Related U.S. Application Data

(60) Provisional application No. 60/513,786, filed on Oct. 23, 2003.

(51) Int. Cl.
  *C07D 209/42* (2006.01)
(52) U.S. Cl. .................... 548/492; 534/790; 546/201; 514/254.09
(58) Field of Classification Search .................. None
  See application file for complete search history.

(56) References Cited

U.S. PATENT DOCUMENTS

| | | | | |
|---|---|---|---|---|
| 4,263,304 A | * | 4/1981 | Ishizumi et al. | ............. 414/262 |
| 5,463,564 A | | 10/1995 | Agrafiotis et al. | |
| 5,684,032 A | | 11/1997 | Elliott et al. | |

FOREIGN PATENT DOCUMENTS

WO    WO 86/00991    2/1986

OTHER PUBLICATIONS

Cawse, J. N. "Experimental Strategies for Combinatorial and High Throughput Materials Development" GE Research & Development Center Technical Information Series Sep. 2000, 1-15.*
Silverman, Richard B. The Organic Chemistry of Drug Design and Drug Action. New York: Academic Press, Inc. 1992, pp. 19-23, especially Table 2.2.*
Tois et al. "Vilsmeier Formylation of 2-Carboxyindoles and Preparation of O-Benzylhydroxyureas on Solid Phase" J. Comb. Chem. 2001, 3, 542-545.*
(Lee at al. "Solid-Phase Rhodium Carbenoid N-H Insertion Reactions: the Synthesis of a Diverse Array of Indoles" J. Comb. Chem. 2003, 5(2), 188-196.*
Lee, Sang-Hyeup, et al., *Solid-Phase Rhodium Carbenoid N-H Insertion Reactions: the Synthesis of a Diverse Array of Indoles*, Journal of Combinatorial Chemisrty, 5(2), pp. 188-196, (2003), XP002323268.
Lee, Sang-Hyeup, et al., *Solid Phase Rhodium Carbenoid N-H Insertion Reactions: the Synthesis of a Diverse Array of Indoles*, Journal of Combinatorial Chemistry, 5(2), Supplementary Information, pp. S1-S16 (2003), XP002323269.

Tois, J., et al., *Solid-Phase Bromination and Suzuki Coupling of 2-Carboxyindoles*, Combinatorial Chemistry and High Throughput Screening, 4(6), pp. 521-524, (2001), XP009045852.
Yamazaki, et al., *Solid-Phase Synthesis of Indolecarboxylates using Palladium-Catalyzed Reactions*, J. Org. Chem, vol. 68, No. 15, pp. 6011-6019 (2003), XP002323296.
Bashiardes, G., et al., *A new method for the Synthesis of Plurisubstituted Pyrroles*, Tetrahedron Letters, Elsevier Science Publishers, Amsterdam NL, vol. 44, No. 46, pp. 8417-8420 (2003), XP004463878.
Bunker, A.M., et al., *1,3-Diaryl-2-Carboxyindoles as Potent Non-Peptide Endothelin Antagonists*, Bioorganic & Medicinal Chemistry Letters, Oxford, GB; vol. 6, No. 9, pp. 1061-1066 (1996), XP004134909.
Mederski, W.W.K.R., et al., *N-Aryl Heterocycles Via Coupling Reactions with Arylboronic Acids*, Tetrahedron, Elsevier Science Publishers, Amsterdam, NL, vol. 55, No. 44, pp. 12757-12770 (1999), XP004180368.
Abreu, A.S., et al., *Synthesis and Intramolecular Cyclization of Novel Beta, Beta-Bis-(benzo 'b!thienyl)dehydroalanine Derivatives*, Tetrahedron Letters, Elsevier Science Publishers, Amsterdam, NL, vol. 44, No. 16, pp. 3377-3379 (2003), XP004417077.
Malapel-Andrieu, B., et al., *Synthesis and Reactivity of Substituted 3-'(Trifluoromethly)sulfony!oxy)-1H-Indole-2-Carboxylate in Palladium-Catalyzed Reactions*, Tetrahedron Elsevier Science Publishers, Amsterdam, NL, vol. 54, No. 37, pp. 11079-11094 (1998), XP004132304.
Liao Y-X, et al., *Efficient Synthesis of Trisubstituted '1!benzopyrando '4,3-b!pyrrol-4(1H)-One derivatives from 4-Hydroxycoumarin*, Tetrahedron Letters, Elsevier Sciense Publishers, Amsterdam, NL, vol. 44, No. 8, pp. 1599-1602 (2003), XP0044205280.
Database Beilstein Beilstein Institut Zur Forderung Der Chemischen Wissenschaften, Frankfurt AM Main, DE; XP002323272, Database Accession No. 298982, 246940, 289846, 272328 Abstract & Huges, et al: J. Proc. R. Soc. N.S.W., vol. 71, pp. 475-482 (1937-1938).
Database Beilstein Beilstein Institut Zur Forderung Der Chemischen Wissenschaften, Frankfurt AM Main, DE; XP002323273, Database Accession No. 9213207, Abstract & Nakamur, et al., Org. Lett., vol. 4, No. 14, pp. 2317-2320 (2002).
Database Beilstein Beilstein Institut Zur Forderung Der Chemischen Wissenschaften, Frankfurt AM Main, DE; XP002323274, Database Accession No. 7965831, Abstract & Fabio, et al.: Synth. Commun., vol. 28, No. 1, pp. 51-60 (1998).
Database Beilstein Beilstein Institut Zur Forderung Der Chemischen Wissenschaften, Frankfurt AM Main, DE; XP002323275, Database Accession No. 7799589, Abstract & Moloney, et al.: J. Med. Chem., vol. 40, No. 15, pp. 2347-2363 (1997).
Database Beilstein Beilstein Institut Zur Forderung Der Chemischen Wissenschaften, Frankfurt AM Main, DE; XP002323276, Database Accession No. 7542064, Abstract & Fuerstner, et al.: Tetrahedron, vol. 52, No. 21, pp. 7329-7344 (1996).
Database Beilstein Beilstein Institut Zur Forderung Der Chemischen Wissenschaften, Frankfurt AM Main, DE; XP002323277, Database Accession No. 7383229, Abstract & Choshi, et al.: J. Org. Chem., vol. 60, No. 18, pp. 5899-5904 (1995).

(Continued)

*Primary Examiner*—Jon D Epperson
(74) *Attorney, Agent, or Firm*—George W. Johnston; Patricia S. Rocha-Tramaloni; David E. Wildman

(57) ABSTRACT

Combinatorial libraries that contains various different 4, 5 fused 3-substituted-2-pyrrolocarboxylic acids for screening pharmacological activity and methods of synthesizing said libraries.

1 Claim, No Drawings

OTHER PUBLICATIONS

Database Beilstein Beilstein Institut Zur Forderung Der Chemischen Wissenschaften, Frankfurt AM Main, DE; XP002323278, Database Accession No. 344331, Abstract & Cook, et al.: J. Chem. Soc, pp. 397-400 (1943).

Database Beilstein Beilstein Institut Zur Forderung Der Chemischen Wissenschaften, Frankfurt AM Main, DE;XP002323279, Database Accession No. 5627914, Abstract & Ishii, et al.: Chem.Pharm.Bull., vol. 31, No. 12 , pp. 4391-4400 (1983).

Database Beilstein Beilstein Institut Zur Forderung Der Chemischen Wissenschaften, Frankfurt AM Main, DE; XP002323280, Database Accession No. 247605, Abstract & Sempronj: Gazz. Chim Ital., vol. 68, pp. 263-268 (1938).

Database Beilstein Beilstein Institut Zur Forderung Der Chemischen Wissenschaften, Frankfurt AM Main, DE; XP002323281, Database Accession No. 1150849, Abstract & Tsuge, et al: Chem. Lett., pp. 1407-1410 (1979).

Database Beilstein Beilstein Institut Zur Forderung Der Chemischen Wissenschaften, Frankfurt AM Main, DE; XP002323282, Database Accession No. 5978943, Abstract & Hirai, et al., J. Med. Chem., vol. 23, No. 7, pp. 764-773 (1980).

Database Beilstein Beilstein Institut Zur Forderung Der Chemischen Wissenschaften, Frankfurt AM Main, DE; XP002323283, Database Accession No. 270866, Abstract & Gabriel, et al., Chem. Ber., vol. 56, p. 1024 (1923).

Database Beilstein Beilstein Institut Zur Forderung Der Chemischen Wissenschaften, Frankfurt AM Main, DE; XP002323284, Database Accession No. 4484374, Abstract & Hiremath, et al., Indian J. Chem. Sect. B, vol. 27, No. 1-12, pp. 756-757 (1988).

* cited by examiner

COMBINATORIAL LIBRARY OF 3-ARYL-1H-INDOLE-2-CARBOXYLIC ACID

PRIORITY TO RELATED APPLICATIONS

This application claims the benefit of Provisional Application Ser. No. 60/513,786, filed Oct. 23, 2003.

TECHNICAL FIELD

This invention is directed to combinatorial chemistry libraries containing 3-aryl-2-indolylcarboxylic acids as well as solid phase methods for constructing such combinatorial chemistry libraries.

BACKGROUND

Modern day drug discovery is a multi-faceted endeavor. Researchers commonly delineate a biochemical pathway that is operative in a targeted pathological process. This pathway is analyzed with an eye toward determining its crucial elements: those enzymes or receptors that, if modulated, could inhibit the pathological process. An assay is constructed such that the ability of the important enzyme or receptor to function can be measured. The assay is then performed in the presence of a variety of molecules. If one of the assayed molecules modulates the enzyme or receptor in a desirable fashion, this molecule may be used directly in a pharmaceutical preparation or can be chemically modified in an attempt to modulate its beneficial activity. The identified molecule that exhibits the best profile of beneficial activity may ultimately be formulated as a drug for the treatment of the targeted pathological process.

With the use of high-throughput screening techniques, one can assay the activity of tens of thousands of molecules per week. Where molecules can only be synthesized one at a time, the rate of molecule submission to an assay becomes a debilitating, limiting factor. This problem has led researchers to develop methods by which large numbers of molecules possessing diverse chemical structures can be rapidly and efficiently synthesized. One such method is the construction of chemical combinatorial libraries.

Chemical combinatorial libraries are diverse collections of molecular compounds. Gordon et al. (1995) *Acc. Chem. Res.* 29:144-154. These compounds are formed using a multi-step synthetic route, wherein a series of different chemical modules can be inserted at any particular step in the route. By performing the synthetic route multiple times in parallel, each possible permutation of the chemical modules can be constructed. The result is the rapid synthesis of hundreds, thousands, or even millions of different structures within a chemical class.

For several reasons, the initial work in combinatorial library construction focused on peptide synthesis. Furka et al. (1991) *Int. J. Peptide Protein Res.* 37:487-493; Houghton et al. (1985) *Proc. Natl. Acad. Sci. USA* 82:5131-5135; Geysen et al. (1984) *Proc. Natl. Acad. Sci. USA* 81:3998; and Fodor et al. (1991) *Science* 25:767. The rapid synthesis of discrete chemical entities is enhanced where the need to purify synthetic intermediates is minimized or eliminated; synthesis on a solid support serves this function. Construction of peptides on a solid support is well known and well documented. Obtaining a large number of structurally diverse molecules through combinatorial synthesis is furthered where many different chemical molecules are readily available. Finally, many peptides are biologically active, making them interesting as a class to the pharmaceutical industry.

The scope of combinatorial chemistry libraries has recently been expanded beyond peptide synthesis. Polycarbamate and N-substituted glycine libraries have been synthesized in an attempt to produce libraries containing chemical entities that are similar to peptides in structure, but possess enhanced proteolytic stability, absorption and pharmacokinetic properties. Cho et al. (1993) *Science* 261:1303-1305; Simon et al. (1992) *Proc. Natl. Acad. Sci. USA* 89:9367-9371. Furthermore, benzodiazepine, pyrrolidine, and diketopiperazine libraries have been synthesized, expanding combinatorial chemistry to include heterocyclic entities Bunin et al. (1992) *J. Am. Chem. Soc.* 114:10997-10998; Murphy et al. (1995) *J. Am. Chem. Soc.* 117:7029-7030; and Gordon et al. (1995) *Biorg. Medicinal Chem. Lett.* 5:47-50.

Substituted indoles are a class of bioactive, heterocyclic molecules that have attracted considerable attention in the pharmaceutical industry. Bunker, Edmunds et al., *Bioorg. Med. Chem. Lett.* 1996, 6(9), 1061-66.

Methods for the solution phase preparation of 3-aryl-2-indolylcarboxylic acids have been reported. Ger. Offenlegungschrift 1,812,205, Sumitomo Chemical Co. ltd.; *Chem. Abstr.*, 71, 124521 F (1969); Zeeh, B. *Chem. Ber.* 1969, 102, 678-685. In this method, two equivalents of an isonitrile are condensed with one equivalent of diarylketone with boron trifluoride catalyst. This route is limited to the production of particularly substituted 3-aryl-2-indolylcarboxylic acids. The solution phase chemistry method also has practical limitations, which hinders the synthesis of thousands of analogs that are possible with a solid phase synthesis approach.

SUMMARY OF THE INVENTION

The present invention is directed to a combinatorial library containing a plurality of different compounds of various structures within the formula:

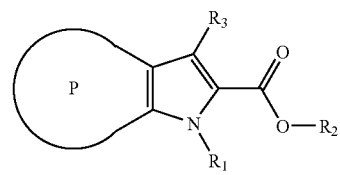

wherein P is a fused ring substituent, which ring substituent is an aromatic ring, a heteroaromatic ring or a cycloaliphatic ring which may be substituted or unsubstituted; $R_2$ is hydrogen or taken together with its attached oxygen atom forms a hydrolyzable ester protecting group, $R_1$ is hydrogen, lower alkyl containing from 1 to 7 carbon atoms, lower alkenyl containing from 3 to 7 carbon atoms, lower alkynyl containing from 3 to. 7 carbon atoms, mono or bicycloaliphatic ring with each ring having from 3 to 7 carbon atoms, aryl containing from 1 to 3 fused aromatic rings with at least one of said rings containing 6 carbon atoms and the other rings containing 5, 6 or 7 carbon atoms, heterocyloaliphatic containing 1 to 2 fused rings with each ring containing from 2 to 6 carbon atoms with one or two hetero atoms selected from the group consisting of O, S and N, monocyclic or bicyclic heteroaryl rings each containing from 1 to 5 carbon atoms with 1 to 4 hetero atoms which can be N, S or O with the proviso that when the hetero atom is S or O, there is 1 hetero atom in the ring and when the hetero atom is N there are from 1 to 4 N atoms in the ring, and wherein the hetero ring in the heterocycloaliphatic ring or monocyclic or bicyclic heteroaryl rings can be condensed with an aryl or cycloaliphatic ring and wherein any of the heteroaryl, aryl, cycloaliphatic or heteroaliphatic rings in the cycloaliphatic, aryl, heteroaryl or heteroaliphatic substituents may be connected to the formula I by a lower alkylene chain containing from 1 to 7 carbon atoms and $R_3$ is a ring substituent selected from the group consisting of an aromatic ring, a heteroaromatic ring and a cycloaliphatic ring which ring substituent may be substituted or unsubstituted.

The library of compounds is prepared by first reacting a compound of the formula:

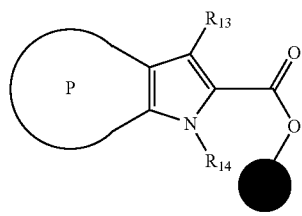
III wherein ● is a solid support, $R_{13}$ is Cl, Br, I or mesyloxy; $R_{14}$ is an amino protecting group or $R_{17}$, and $R_{17}$ is $R_1$ other than hydrogen and $R_2$, $R_1$ and P are as above, with a boronic acid of the formula:

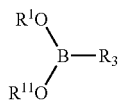
V wherein $R_3$ is as above $R^1$ and $R^{11}$ are individually lower alkyl or taken together form a lower alkylene bridge between their attached oxygen atoms, to produce an immobilized compound of the formula:

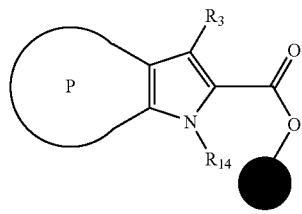
IV wherein ●, P, $R_{14}$, $R_2$, and $R_3$ are as above.

The compound of formula IV can be cleaved by the methods mentioned hereinafter, such as hydrolysis, acidic elimination or photolytic cleavage, from the solid support to produce the compound of formula I as a free acid which can be converted to a hydrolyzable ester by conventional means.

In this manner a series of different compounds of the formula I can be easily produced with various boronic acids of formula V to build up a combinatorial library.

DETAILED DESCRIPTION

The present invention provides a combinatorial library that contains various different 4,5-fused-3-substituted-2-pyrrolo-carboxylic acids, where the P ring is an aromatic ring, a heteroaromatic ring, an aliphatic ring or substituted versions thereof, of the formula:

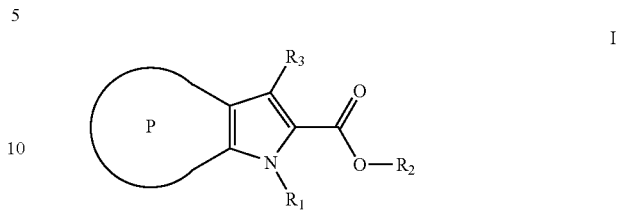
I wherein P, $R_1$, $R_2$ and $R_3$ are as above.

In one embodiment, the chemical method for the production of combinatorial library compounds contains methodology for the solid phase synthesis of 3-substituted-2-indolyl-carboxylic acids. The compounds which make up the library include but are not limited to the following:

$R_1$-3-$R_3$-1H-indole-2-carboxylic acid
7-$R_1$-5-$R_3$-7H-pyrrolo[2,3-d]pyrimidine-6-carboxylic acid
5-$R_1$-7-$R_3$-5H-pyrrolo[3,2-d]pyrimidine-6-carboxylic acid
$R_1$-3-$R_3$-1H-pyrrolo[3,2-c]pyridine-2-carboxylic acid
$R_1$-3-$R_3$-1H-pyrrolo[2,3-c]pyridine-2-carboxylic acid
$R_1$-3-$R_3$-1H-pyrrolo[2,3-b]pyridine-2-carboxylic acid
$R_1$-3-$R_3$-1H-pyrrolo[3,2-b]pyridine-2-carboxylic acid
5-$R_1$-7-$R_3$-5H-pyrrolo[2,3-b]pyrazine-6-carboxylic acid
$R_1$-3-$R_3$-1H-pyrrolo[2,3-d]pyridazine-2-carboxylic acid
6-$R_1$-4-$R_3$-6H-thieno[2,3-b]pyrrole-5-carboxylic acid
6-$R_1$-4-$R_3$-6H-furo[2,3-b]pyrrole-5-carboxylic acid
4-$R_1$-6-$R_3$-4H-furo[3,2-b]pyrrole-5-carboxylic acid
4-$R_1$-6-$R_3$-4H-thieno[3,2-b]pyrrole-5-carboxylic acid In accordance with various embodiments of this invention, for 1-$R_1$-3-$R_3$-1H-indole-2-carboxylic acid, 7-$R_1$-5-$R_3$-7H-pyrrolo[2,3-d]pyrimidine-6-carboxylic acid, 5-$R_1$-7-$R_3$-5H-pyrrolo[3,2-d]pyrimidine-6-carboxylic acid, 1-$R_1$-3-$R_3$-1H-pyrrolo[3,2-c]pyridine-2-carboxylic acid, 1-$R_1$-3-$R_3$-1H-pyrrolo[2,3-c]pyridine-2-carboxylic acid, 1-$R_1$-3-$R_3$-1H-pyrrolo[2,3-b]pyridine-2-carboxylic acid, 1-$R_1$-3-$R_3$-1H-pyrrolo[3,2-b]pyridine-2-carboxylic acid, 5-$R_1$-7-$R_3$-5H-pyrrolo[2,3-b]pyrazine-6-carboxylic acid, 1-$R_1$-3-$R_3$-1H-pyrrolo[2,3-d]pyridazine-2-carboxylic acid, 6-$R_1$-4-$R_3$-6H-thieno[2,3-b]pyrrole-5-carboxylic acid, 6-$R_1$-4-$R_3$-6H-furo[2,3-b]pyrrole-5-carboxylic acid, 4-$R_1$-6-$R_3$-4H-furo[3,2-b]pyrrole-5-carboxylic acid, 4-$R_1$-6-$R_3$-4H-thieno[3,2-b]pyrrole-5-carboxylic acid where $R_4$, $R_5$, $R_6$, and $R_7$ can independently be alkyl, aryl, heteroaryl, and electron withdrawing groups. Preferably, the combinatorial library contains a 4,5-fused-3-substituted-2-pyrrolocarboxylic acid including but not limited to 1-$R_1$-3-$R_3$-1H-indole-2-carboxylic acid.

The chemical combinatorial library of this invention containing plurality of different compound of formula I can be screened for various pharmacological activities. The compounds of formula I have activity as antagonists against chemoattractant receptors such as chemotine receptors, particularly antagonists against the CCR6 receptor. The combinatorial chemical library of this invention can be screened against such chemoattractant receptors such as CCR6 utilizing the cell migration assay disclosed in PCT publication WO 02/101350 A2 published on Dec. 19, 2002. Antagonists against CCR6 are useful as anti-inflammatory agents.

A chemical library is an intentionally created collection of different molecules which can be prepared synthetically and screened for biological activity in a variety of different formats. The library may consist of the soluble molecules themselves or the library can consist of libraries of such molecules bound to a solid support. In both types of formats the combinatorial library of this invention can be screened. The libraries of this invention contain at least two different compounds within the compound of formula I. In general the libraries of this invention should contain at least 150 different compounds having the structure of Formula I with libraries of from 200 to 1,000 different compounds being preferred. The method of this invention allows one to create a library containing different molecules of the compounds having the formula of formula I. The synthetic chemical route of this invention is ideally suited for mass producing a library of different compounds having the structure of formula I.

Libraries of this invention can be randomized by being deliberately prepared utilizing standard randomization procedures. By these procedures different compounds of formula I, without the $R_1$ and $R_3$ substituents can be connected to a solid support and reacted with a cocktail of a mixture of different reagents producing different $R_1$ and $R_3$ substituents on the molecule bound to the solid support. The reactions are allowed to proceed so that on each compound on the solid support member is reacted with one of the reactants in this randomized mixture of the reactants. In this manner, a different $R_1$ and $R_3$ group will be placed on each of the various molecules attached to a solid residence support. On the other hand where the library is deliberately prepared specific reactants which give one specific one $R_1$ and $R_3$ substituent are utilized rather than a randomized cocktail of reagents. These specific reagents are specifically geared to producing a given compound on the solid support containing the compound which does not contain any $R_1$ or $R_3$ substituent.

As used herein, the term halogen, halo or halide designates all four halogens such as chlorine, bromine, fluorine or iodine. The term lower alkyl designates a saturated monovalent hydrocarbon substituent containing from 1 to 7 carbon atoms such as for example, methyl, ethyl, n- or iso-propyl or n-, sec-, or tert-butyl or a straight-chain or branched pentyl, hexyl, heptyl substituent. The term lower alkenyl designates an olefinic unsaturated monovalent hydrocarbon substituent containing from 3 to 7 carbon atoms and from 1 to 2 olefinic unsaturated double bonds such as allyl, 2- or 3-butenyl, isobutenyl or n-penta-2,4-dienyl. The term lower alkynyl designates a monovalent aliphatic acetylenically unsaturated hydrocarbon, containing from 3 to 7 carbon atoms such as propagyl. The term cycloaliphatic ring designates a monocyclic or bicyclic aliphatic hydrocarbon ring which can be a cyclo lower alkyl or cyclo lower alkenyl ring containing from 3 to 7 carbon atoms. The preferred cyclo lower alkyl ring is a cyclopropyl, dimethylcyclopropyl, cyclobutyl, cyclopentyl or cyclohexyl ring and the preferred cyclo lower alkenyl ring is cyclo pentadienyl or cyclohexenyl ring. The bicyclo alkyl rings consist of two fused alkyl rings, each containing from 3 to 6 carbon atoms such as for example, bornyl or norbornyl.

The term heterocycloaliphatic designates a monovalent cycloaliphatic ring containing from 2 to 6 carbon atoms in the ring with these carbon atoms being interrupted with one or two hetero atoms selected from the group O, S or N. The term aryl designates an aromatic hydrocarbon moiety having from 1, 2 or 3 rings with at least one ring containing 6 carbon atoms and the other rings containing 5, 6 or 7 carbon atoms. Where aryl consists of 2 or 3 rings, all of the rings which make up the aryl substituent are fused, which each ring containing 5, 6 or 7 carbon atoms. The preferred aryl substituents, other than phenyl, are naphthyl or indenyl.

In accordance with this invention, the term heteroaryl designates mono- or bicyclic heteroaryl rings each containing from 2 to 6 carbon atoms with 1 to 3 hetero atoms and the hetero atoms in each ring being N, S or O with the proviso that when the hetero atom is S or O, there is 1 hetero atom in the ring and when the hetero atoms is N, there are from 1 to 4 nitrogen atoms in the ring. In accordance with this invention, it is preferred when there are 2 or more hetero atoms in the ring that the hetero atoms be all nitrogen, oxygen or sulfur. Further, in accordance with this invention, the hetero ring in the heterocycloaliphatic or heteroaryl substituent can be fused or condensed with an aryl or cycloaliphatic ring such as defined herein. The preferred aryl is phenyl and the preferred cycloaliphatic rings which are fused with the heteroatom generally should contain only 1 cycloaliphatic ring.

Furthermore, in accordance with this invention, the heteroaryl, cycloaliphatic and heterocyclic ring, when these groups constitute $R_1$ and $R_2$ can be connected to their respective N atoms on the compound of formula I by a lower alkylene chain containing from 1 to 7 carbon atoms. The term lower alkylene designated a bivalent saturated hydrocarbon group containing from 1 to 7 carbon atoms. Preferably, the hydrocarbon chain of lower alkylene is a straight-chain which contains a free valence at both the terminal carbon atoms in the chain such as methylene, 1,2-ethylene, 1,3-propylene and 1,4-butylene.

When $R_1$, $R_2$, $R_3$ and P contain aromatic, heteroaromatic or a cycloaliphatic rings, these rings may be substituted or unsubstituted with various substituents, particularity with functional groups or derivativized functional groups. Those functional groups or derivatized functional groups can be amino, $C_1$-$C_4$ alkylamino, di-$C_1$-$C_4$ alkylamino, hydroxy, can be oxo, thio, nitro, carboxy, carbamoyl, sulfo, sulfamoyl, ammonio, amidino, cyano, formylamino, formamido, and halogen or are saturated or unsaturated, aliphatic, cycloaliphatic or heterocycloaliphatic radicals, carboycyclic or heterocyclic aryl radicals, or condensed carbocyclic, hetero cyclic or carbocyclic-heterocyclic radicals, which may themselves be combined as desired with further such radicals and substituted by the mentioned functional groups or derivatized functional groups. The mentioned substituents and radicals may also be interrupted by one or more bivalent radicals from the group —O—, —S—, —C(=O)O—, —O—C(C=O)—, —C(=O)—N($C_1$-$C_4$alkyl)-, —N($C_1$-$C_4$alkyl)-C(=O)—, —S(=O)—, —S(=O)$_2$, —S(=O)—O—, S(O)$_2$—, —S(=O)—N($C_1$-$C_4$alkyl)-, —S(=O)$_2$—N($C_1$-$C_4$alkyl)-, —($C_1$-$C_4$alkyl)N—S(=O)—, —($C_1$-$C_4$alkyl)N—S(=O)$_2$—, —P(=O)—, —P(=O)—O—, —O—P(=O)—, and —O—P(=O)—.

In accordance with an embodiment of this invention, the library may contain a plurality of different compounds selected from compounds of the formula:

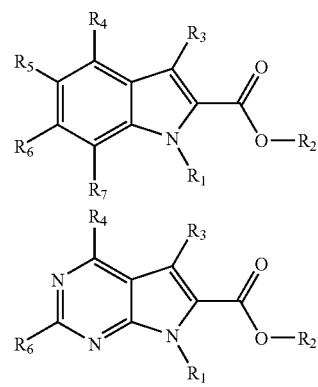

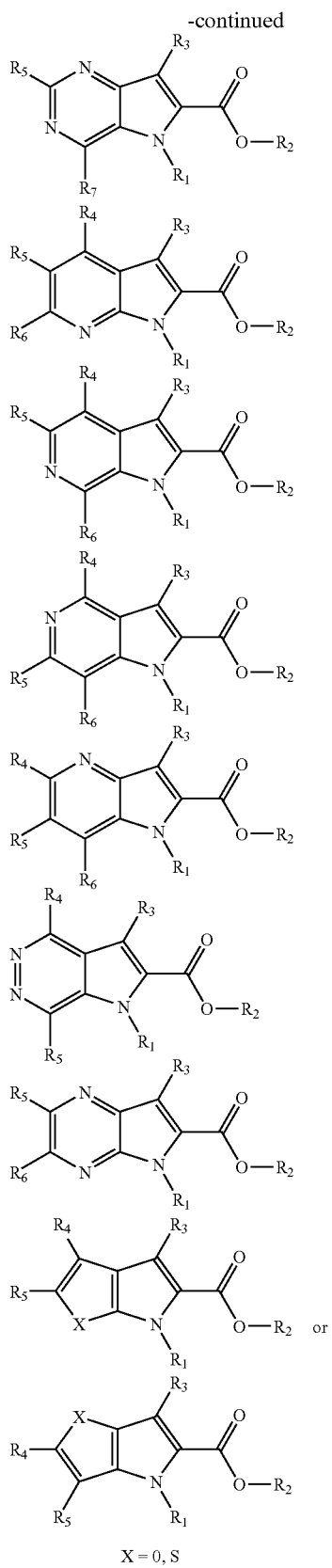

wherein $R_1$, $R_2$ and $R_3$ are as above; and $R_4$, $R_5$, $R_6$ and $R_7$ are individually selected from functional groups or derivatized functional groups consisting of amino, $C_1$-$C_4$alkylamino, di-$C_1$-$C_4$ alkylamino, hydroxy, oxo, thio, nitro, carboxy, carbamoyl, sulfo, sulfamoyl, ammonio, amidino, cyano, formylamino, formamido, halogen, saturated or unsaturated, cycloalkyl, heterocycloalkyl, aryl, or heteroaromatic rings which may be condensed with aryl, heteroaromatic or heterocycloalkyl rings and X is O or S.

In accordance with another embodiment of this invention, the library may contain a plurality of different compounds where $R_3$ is selected from the group consisting of

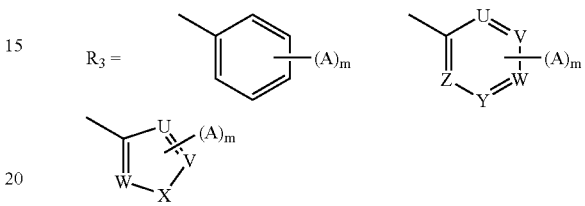

wherein m is an integer of from 1 to 5, A is $R_4$, $R_5$, $R_6$ and, $R_7$ and U, V, W, Y and Z are individually —N— or —CH—, X is O or S.

Suitable substituents A from the group $R'_1$, $R'_2$, $R'_3$, $R'_4$, and $R'_5$ are especially functional groups from the group consisting of amino, $C_1$-$C_4$ alkylamino, for example methyl- or ethyl-amino, di-$C_1$-$C_4$ alkylamino, for example dimethyl- or diethyl-amino, hydroxy, oxo, thio, nitro, carboxy and halogen, or are substituents from the group lower alkyl, lower alkenyl, lower alkynyl, monocycloalkyl, bicycloalkyl, cycloalkenyl, heterocycloalkyl, aryl, heteroaryl, carbocyclic $C_7$-$C_{16}$ aralkyl and heteroarylalkyl, which may themselves be substituted by the mentioned functional groups and interrupted by the mentioned bivalent radicals.

Lower alkyl is, for example, methyl, ethyl, n- or iso-propyl or n-, sec- or tert-butyl or straight chain or branched pentyl, hexyl.

Lower alkenyl is, for example, vinyl, allyl, 2-or 3-butenyl, isobutenyl or n-penta-2,4-dienyl.

Lower alkynyl is, for example, 1- or 2-propynyl.

Monocycloalkyl is, for example, cyclopropyl, dimethylcyclopropyl, cyclobutyl, cyclopentyl or cyclohexyl.

Bicycloalkyl is, for example, bornyl or norbornyl.

Cycloalkenyl is, for example, cyclopentadienyl or cyclohexenyl.

Heterocycloalkyl preferably contains 2 to 5 carbon atoms and one or two hetero atoms from the group O, S and N. Examples are the substituents derived from oxirane, azirine, 1,2-oxathiolane, pyrazoline, pyrrolidine, piperidine, piperazine, morpholine, tetrahydrofuran or tetrahydrothiophene.

Aryl is, for example, mono-, bi- or tri-cyclic, for example phenyl, naphthyl, indenyl.

Heteroaryl is preferably monocyclic or condensed with a further heterocycle or with an aryl radical, for example, phenyl, and preferably contains one or two, and in the case of nitrogen up to four, hetero atoms from the group O, S and N. Suitable substituents are derived from furan, thiophene, pyrrole, pyridine, bipyridine, picolylimine, γ-pyran, γ-thiopyran, phenanthroline, pyrimidine, bipyrimidine, pyrazine, indole, coumarone, thionaphthene, carbazole, dibenzofuran, dibenzothiophene, pyrazole, imidazole, benzimidazole, oxazole, thiazole, dithiazole, isoxazole, isothiazole, quinoline, isoquinoline, acridine, chromene, phenazine, phenoxazine, phenothiazine, triazine, thianthrene, purine or tetrazole.

Aralkyl preferably contains from 7 to 12 carbon atoms, for example, benzyl, 1- or 2-phenethyl or phenylpropyl.

Heteroarylalkyl preferably consists of the mentioned heterocycles, which substitute, for example, $C_1$-$C_4$ alkyl radicals, where possible in the terminal position, but also in the adjacent position (1-position) or in the alpha-position (2-position), depending upon the length of the carbon chain.

"Amino protecting group" refers to a chemical group that exhibits the following characteristics: (1) reacts selectively with the desired amino in good yield to give a protected substrate that is stable to the projected reactions for which protection is desired; 2) is selectively removable from the protected substrate to yield the desired functionality; and 3) is removable in good yield by reagents compatible with the other functional group(s) generated in such protected reactions. Examples of amino protecting groups can be found in Greene et al. (1991) *Protective Groups in Organic Synthesis*, $2^{nd}$ Ed. (John Wiley & Sons, Inc., New York).

When $R_2$ taken together with its attached oxygen atom forms a hydrolyzable ether protecting group, the ether protecting group can be any conventional hydrolyzable ether protecting group such as described in the aforementioned Greene et al. publication. These protecting groups do not affect the activity of the compound of formula I above. In accordance with this invention, these esters can be produced by reacting by conventional means the compound of formula I with $R_2$ being hydrogen with the active form of the acid protecting group that one wishes to form on the molecule of formula I. The preferred active forms are the alcohols or the halides of these hydrolyzable ether protecting groups. Generally among the preferred groups are the lower alkyl esters or the aryl esters such as benzyl or benzyl substituted with a lower alkyl halo, nitro substituent.

In accordance with this invention, any conventional amino protecting group that can be removed by hydrogenolysis, acidic elimination or hydrolysis can be utilized. Among the preferred amino protecting which can be utilized in accordance with this invention are trityl, benzyl, o-nitro benzyl, aromatic urethane-type protecting groups, such as benzyloxycarbonyl (Cbz) and substituted benzyloxycarbonyl, such as p-chlorobenzyloxycarbonyl, p-nitrobenzyloxycarbonyl, p-bromobenzyl-oxycarbonyl, p-biphenyl-isopropyloxycarbonyl, 9-fluorenylmethyl-oxycarbonyl (Fmoc) and p-methoxybenzyloxycarbonyl (Moz); aliphatic urethane-type protecting groups, such as t-butyloxycarbonyl (BOC), diisopropylmethyloxycarbonyl, isopropyloxycarbonyl, and allyloxycarbonyl. Boc is most preferred for amino protection.

In accordance with this invention $R_{13}$ can be Cl, Br, I or mesyloxy.

Combinatorial library synthesis is typically performed on a solid support. See, for example, Lam et. al. (1991) *Nature* 354:82-84; Houghton et al. (1991) *Nature* 354:84-86. A large number of beads or particles are suspended in a suitable carrier (such as a solvent) in a parent container. The beads, for example, are provided with a functionalized point of attachment for a chemical module. The beads are then divided and placed in various separate reaction vessels. The first chemical module is attached to the bead, providing a variety of differently substituted solid supports. Where the first chemical module includes 3 different members, the resulting substituted beads can be represented as $A_1$, $A_2$, and $A_3$.

The beads are washed to remove excess reagents and subsequently remixed in the parent container. This bead mixture is again divided and placed into various separate reaction vessels. The second chemical module is coupled to the first chemical module. Where the second chemical module includes 3 different members, $B_1$, $B_2$, and $B_3$, 9 differently substituted beads result: $A_1$-$B_1$, $A_1$-$B_2$, $A_1$-$B_3$, $A_2$-$B_1$, $A_2$-$B_2$, $A_2$-$B_3$, $A_3$-$B_1$, $A_3$-$B_2$, and $A_3$-$B_3$. Each bead will have only a single type of molecule attached to its surface.

The remixing/redivision synthetic process can be repeated until each of the different chemical modules has been incorporated into the molecule attached to the solid support. Through this method, large numbers of individual compounds can be rapidly and efficiently synthesized. For instance, where there are 4 different chemical modules, and where each chemical module contains 20 members, 160,000 beads of different molecular substitution can be produced.

Combinatorial library synthesis can be performed either manually construction of a combinatorial library, a scientist would perform the various chemical manipulations. For the construction of a combinatorial library through an automated process, the various chemical manipulations will typically be performed robotically. For example, see U.S. Pat. No. 5,463,564.

The synthesis of a 3-aryl, 2-carboxy indole compound library can be performed on a solid support. "Solid support" includes an insoluble substrate that has been appropriately derivatized such that a chemical molecule can be attached to the surface of the substrate through standard chemical methods. Solid supports include, but are not limited to, beads and particles, such as peptide synthesis resins. For example, see Merrifield (1963) *J. Am. Chem. Soc.* 85:2149-2154; U.S. Pat. No. 4,631,211; and Geysen et al. (1984) *Proc. Natl. Acad. Sci. USA* 81:3998-4002.

Solid supports can consist of many materials, limited primarily by the capacity of the material to be functionalized through synthetic methods. Examples of such materials include, but are not limited to, polymers, plastics, resins polysaccharides, silicon or silica based materials, carbon, metals, inorganic glasses and membranes. Preferred resins include Sasrin resin (a polystyrene resin available from Bachem Bioscience, Switzerland), and TentaGel S AC, TentaGel PHB, or TentaGel S $NH_2$ resin polystyrene-polyethylene glycol copolymer resins available from Rapp Polymere, Tubingen, Germany).

The solid support can be purchased with suitable functionality already present such that a chemical module can be attached to the support surface (e.g., Novabiochem, Argonaut ArgoGel, Bachem Bioscience, Rapp Polymere). Alternatively, the solid support can be chemically modified such that a chemical module can be attached to the support surface. Grant (1992) *Synthetic Peptides. A User's Guide*, W. H Freeman and Co; Hermkens et al. (1996) *Tetrahedron* 52:4527-4554. The choice of functionality used for attaching a molecule to the solid support will depend on the nature of the compound to be synthesized and the type of solid support. Examples of functionality present on the solid support that can be used to attach a chemical module include, but are not limited to, alkyl or aryl halides, aldehydes, alcohols, ketones, amines sulfides, carboxyl groups, aldehyde groups, and sulfonyl groups.

Preferably, the functional group on the solid support that permits the attachment of a chemical module will be an alcohol, or a diol groups. See Gordon et al. (1994) *J. Med. Chem.* 37:1385-1401; Hermkens et al. (1996) *Tetrahedron* 52:4527-4554.

Preferably, the reaction used to attach the chemical module to the solid support will be an esterification of an acid to hydroxy-containing solid phase polymer resin.

To construct a 3-aryl-2-carboxy N1-substituted pyrroles library through the immobilized ester derivative route, a chemical module containing a terminal alcohol, or protected terminal alcohol is attached to a solid support containing functionalized resin. Where the terminal alcohol of the chemical molecule is protected, the synthetic route proceeds through the deprotection of the terminal alcohol.

A solid support bound through a functionalized resin to a fused 3-aryl-2-carboxy N1-substituted pyrroles library can be recovered through conventional methods such as filtration or centrifugation. Confirmation that the solid support contains the desired fused 3-aryl-2-carboxy N1-substituted pyrroles compound can be accomplished by cleaving the fused 3-aryl-2-carboxy N1-substituted pyrroles from a small portion of the solid support, and then subjecting the cleaved product to conventional analysis. Examples of commonly used analytical methods include, but are not limited to, nuclear magnetic resonance spectroscopy and high performance liquid chromatography.

In one embodiment of the invention, the fused 3-aryl-2-carboxy N1-substituted pyrroles library is bound to a solid support. In another embodiment of the invention, the fused 3-aryl-2-carboxy N1-substituted pyrroles are cleaved from the solid support to produce soluble fused 3-aryl-2-carboxy N1-substituted pyrroles libraries. Soluble libraries can be advantageous for a variety of purposes, including assaying the biological activity of compounds and performing structural analysis of compounds.

The cleavage of compounds from a solid support to produce a soluble chemical library can be accomplished using a variety of methods. For example, a compound can be photolytically cleaved from a solid support (Wang et al. (1976) *J. Org. Chem* 41:3258; Rich et al. (1975) *J. Am. Chem. Soc.* 97:1575-1579). Preferably, the cleavage of compounds from a solid support to produce a soluble chemical library is accomplished using hydrolytic conditions, such as through the addition of dilute trifluoroacetic acid.

The present invention is directed toward the generation of fused 3-aryl-2-carboxy N1-substituted pyrroles libraries. These libraries are used to select one or more fused 3-aryl-2-carboxy N1-substituted pyrroles species that demonstrate a specific interaction with a targeted cellular ligand including, but not limited to, enzymes or receptors. A cellular ligand is targeted when it is believed that the ligand is of importance in the modulation of a disease. Examples of disease states for which fused 3-aryl-2-carboxy N1-substituted pyrroles libraries can be screened include, but are not limited to, inflammation, infection, hypertension, CNS disorders, and cardiovascular disorders.

Several methods have been developed in recent years to screen libraries of compounds to identify the compounds having the desired characteristics. Typically, where a compound exhibits a dissociation constant of $10^{-6}$ or less when combined with the targeted enzyme or receptor, the compound is thought to demonstrate a specific interaction with the enzyme or receptor. Methods for isolating library compound species that demonstrate desirable affinity for a receptor or enzyme are well-known in the art. For example, an enzyme solution may be mixed with a solution of the compounds of a particular combinatorial library under conditions favorable to enzyme-ligand binding. See Bush et al. (1993) *Antimicrobial Agents and Chemotherapy* 37:851-858, and Daub et al. (1989) *Biochemistry* 27:3701-3708. Specific binding of library compounds to the enzyme may be detected by any of the numerous enzyme inhibition assays which are well known in the art. Compounds which are bound to the enzyme may be readily separated from compounds which remain free in solution by applying the solution to a Sephadex G-25 gel filtration column. Free enzyme and enzyme-ligand complexes will pass through the column quickly, while free library compounds will be retarded in their progress through the column. The mixture of enzyme-ligand complex and free enzyme can then be treated with a powerful denaturing agent, such as guanidinium hydrochloride or urea, to cause release of the ligand from the enzyme. The solution can then be injected onto an HPLC column (for example, a Vydac C-4 reverse-phase column, eluted with a gradient of water and acetonitrile ranging from 0% acetonitrile to 80% acetonitrile). Diode array detection can provide discrimination of the compounds of the combinatorial library from the enzyme. The compound peaks can then be collected and subjected to mass spectrometry for identification.

An alternate manner of identifying compounds that inhibit an enzyme is to divide the library into separate sub-libraries where one step in the synthesis is unique to each sub-library. To generate a combinatorial library, reactants are mixed together during a step to generate a wide mixture of compounds. At a certain step in the synthesis, however, the resin bearing the synthetic intermediates can be divided into several portions, with each portion then undergoing a unique transformation. The resin portions are then separately subjected to the rest of the synthetic steps in the combinatorial synthetic method. Each individual resin portion thus constitutes a separate sub-library. When testing the compounds, if a given sub-library shows more activity than the other sub-libraries, the unique step of that sub-library may then be held fixed. The sub-library then becomes the new library, with that step fixed, and forms the basis for another round of sub-library synthesis, where a different step in the synthesis is optimized. This procedure can be executed at each step until a final compound is arrived at. The aforementioned method is the generalization of the method described in Geysen, WO 86/00991, for determining peptide "mimotopes," to the synthetic method of this invention.

Finding a compound that inhibits an enzyme is most readily performed with free compound in solution. The compounds can also be screened while still bound to the resin used for synthesis; in some applications, this may be the preferable mode of finding compounds with the desired characteristics. For example, if a compound that binds to a specific antibody is desired, the resin-bound library of compounds may be contacted with an antibody solution under conditions favoring a stable antibody-compound-resin complex. A fluorescently labeled second antibody that binds to the constant region of the first antibody may then be contacted with the antibody-compound-resin complex. This will allow identification of a specific bead as carrying the compound recognized by the first antibody binding site. The bead can then be physically removed from the resin mixture and subjected to mass spectral analysis. If the synthesis has been conducted in a manner such that only one compound is likely to be synthesized on a particular bead, then the binding compound has been identified. If the synthesis has been carried out so that many compounds are present on a single bead, the information derived from analysis can be utilized to narrow the synthetic choices for the next round of synthesis and identification.

The enzyme, antibody, or receptor target need not be in solution either. Antibody or enzyme may be immobilized on a column. The library of compounds may then be passed over the column, resulting in the retention of strongly binding compounds on the column after weaker-binding and non-binding compounds are washed away. The column can then be washed under conditions that dissociate protein ligand binding, which will remove the compounds retained in the initial step. These compounds can then be analyzed, and synthesized separately in quantity for further testing. Similarly, cells bearing surface receptors can be expressed on a cell surface may be contacted with a solution of library compounds. The cells bearing bound compounds can be readily separated from the solution containing non-binding compounds. The cells can then be washed with a solution which will dissociate the bound ligand from the cell surface receptor. Again, the cells can be separated from the solution.

In accordance with a preferred embodiment of this invention, the solid support contains hydroxy group so that it is easily acylated to produce the compound to formula IX. Any conventional means of esterification can be used to react the solid support containing a hydroxy group with the acid of formula VII to produce the compound to formula IX.

In accordance with this invention the compound of formula IX is converted to the compound of formula I above, where $R_1$ is other than hydrogen by the following procedure:

coupling said immobilized alcohol of formula IX to an organic acid of the formula:

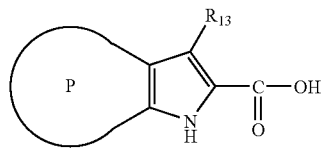

II wherein P, is as above, and $R_{13}$ is Cl, Br, I or mesyloxy, to produce a immobilized ester of the formula:

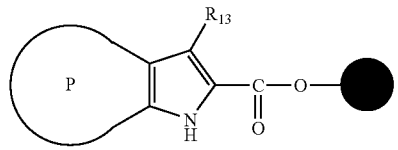

X wherein ●, P, and $R_{13}$ are as above, reacting the compound of formula X with a substituent reagent of the formula $R_1LG$  XI wherein $R_1$ is as above other than hydrogen and LG is a leaving group to produce a compound of the formula

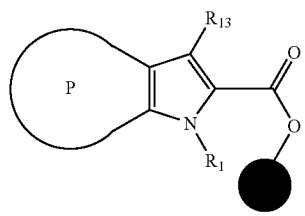

XII wherein ●, P, $R_1$, and $R_{13}$ are as above and $R_1$ is other than hydrogen reacting said indole of formula XII with a boronic acid of the formula

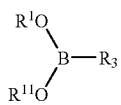

V wherein $R_3$ is as above, $R^1$ and $R^{11}$ are individually lower alkyl or taken together form a lower alkylene bridge between their attached oxygen atoms, to produce an immobilized compound of the formula I where $R_1$ is other than hydrogen of the formula:

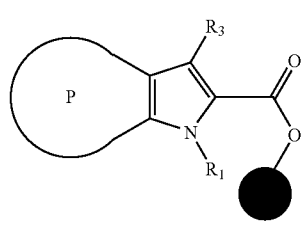

XIII wherein ●, P, and $R_3$ are as above and $R_1$ is as above other than hydrogen, and cleaving by acidic elimination or hydrolysis said immobilized compound of formula XIII from said solid support to produce the compounds of formula I where $R_2$ is hydrogen.

The coupling reaction of the alcohol of formula IX with the organic acid of formula II is carried out to produce the immobilized ester of formula X by utilizing any conventional method of reacting a organic acid with an alcohol to produce ester. In carrying out this reaction, any of the conditions conventional in peptide synthesis can be utilized. Generally this coupling reaction takes place in the presence of a coupling reagent such as dicyclohexylcarbodiimide. Any of the conventional conditions utilized in ester synthesis can be utilized to condense the compound of formula II with the compound of formula IX to produce the ester of formula X.

In the next step, the amino group at the 1-position on the indole ring of the compound of formula X is reacted with the halide of formula XI to produce the compound of formula XII. Any conventional method of condensing an amine with a halide so as to convert a secondary amine to a tertiary amine can be utilized in this synthesis. The reaction of the halide of formula XI is used where one wants to prepare compounds of formula X where $R_1$ is other than hydrogen and produce the compounds of formulae XII and I where at the 1-position on the indole ring, $R_1$ is other than hydrogen. On the other hand, if it is desired to produce a compound of formula I where at the 1-position on the indole ring $R_1$ is hydrogen, then it is necessary to protect the nitrogen with a suitable amino protecting group. Any of the conventional amino protecting groups can be utilized and any method conventional in protecting a secondary amine with a protecting group such as BOC can be utilized. In accordance with this invention, any conventional amino protecting group can be utilized for this purpose of producing a compound to formulae I and XII where $R_1$ is hydrogen.

In the next step of this synthesis, the compound of formula XII, where either $R_1$ is not hydrogen or where $R_1$ is replaced by a conventional amino protecting group, is reacted with a boronic acid of the formula V to produce the compound of formula XIII. In the case where, at the 1-position on the indole ring, $R_1$ is replaced by an amino protecting group in the compound of formula XII, this amino protecting group will also be at the 1-position in the compound of formula XIII. In accordance with this invention, the amino group at the 1-position of indole ring in the compound of formula XII should not contain a hydrogen substituent in this reaction. The reaction of the compound of the formula XII with a compound of formula IV is carried out by utilizing a Suzuki coupling reactions, such as disclosed by S. S. Bhawgwat et al. *Tetrahedron Lett.* 1994, 35 p. 1847-1850. In carrying out this reaction, any of the conditions conventional in a Suzuki reaction can be utilized. Generally, these reactions are carried out in the presence of a metal catalyst such as a palladium catalyst utilizing any conventional organic solvent and a weak inorganic base. Among the preferred organic solvents are the polar aprotic solvents. Any conventional polar aprotic solvents can be utilized in carrying out this invention. Suitable solvents are customary, especially higher-boiling, solvents, for example, non-polar aprotic solvents, e.g., xylene or toluene, or polar aprotic solvents, e.g., dimethoxyethane. The weak inorganic base can be carbonates or bicarbonates, such as potassium carbonate, and cesium carbonate. In this manner by either placing a substituent on or protecting the nitrogen atom at the 1-position on the indole ring, one can easily produce the compound of formula XIII utilizing the Suzuki reaction with the boronic acid of formula VI.

In the coupling reaction involving the compound of formula V with the compound of formula XII, the leaving group is eliminated. In the coupling reaction, especially in the Suzuki reaction, suitable leaving groups are, for example, halogen, e.g., chlorine, bromine or iodine, or an organosulfonyloxy radical, for example, mesyloxy. Iodine is the preferred leaving group in the Suzuki type reactions. Coupling reactions of the Suzuki type occur with excellent yield and high purity.

A preferred embodiment of the Suzuki type reaction utilizes a palladium catalyst and a substituted aryl chloride deactivated by means of electron-rich or electron-repelling groups. The "catalytic amounts" of the palladium type catalyst preferably denotes an amount of from approximately 0.0001 to 5.0 mol %, especially from 0.001 to 1.0 mol %, based on the amount of the substrate used. The molar ratio of the reaction partners of the Suzuki coupling reaction of the boronic acid derivative of formula V to the compound of formula XII is generally in the range of from 1:1 to 1:10, a ratio in the range of from 1:1 to 1:2 being preferred. In carrying out this reaction, temperature and pressure are not critical, however, it is preferred that this reaction take place with cooling up to the boiling temperature of the solvent, especially from room temperature to the boiling temperature of the solvent (reflux conditions). Working up and isolation of the obtainable reaction product are effected in a manner known in the art using customary purification methods, for example, removal of the solvent and subsequent separation methods, e.g., fine distillation, re-crystallization, preparative thin-layer chromatography, column chromatography, preparative gas chromatography, etc.

In accordance with this procedure, compounds of formula III, IV and XIII can be cleaved from the resin support by any of the methods above. Generally, it is preferred to cleave these compounds by acidic elimination utilizing a strong acid or trifluoroacetic acid, or mineral acids. Any conventional method of cleaving esters from the solid support such as used in solid peptides synthesis can be employed in the process of this invention. In this manner, the compounds will be cleaved from their solid support and where the nitrogen at the 1-position in the indole ring contains an amino protecting group, this amino protecting group will be eliminated or hydrolyzed under the acid conditions to produce the compound of formula I where $R_1$ and $R_2$ are hydrogen. If one desires to produce the compound of formula III where $R_{14}$ is hydrogen, then an amino protecting group which can be removed hydrogenolysis is chosen to be the protecting group at the 1-position on the indole ring. By removing this amino protecting group by hydrogenolysis, the solid support will remain connected to the molecule. Hence, removal of the amino protecting group can be accomplished without cleaving the solid support. In this manner, the compound of formula III, where $R_{14}$ is hydrogen is produced.

In accordance with this invention, the organic acid of formula II is prepared from the compound of the formula

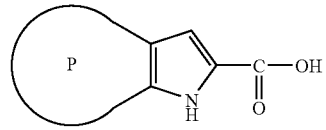

XV by placing a leaving group such as disclosed hereinbefore and the 3-position of the indole ring. The 3-position is particularly reactive to the placement of a leaving group as a substituent at this position. The preferred leaving group is halide, particularly an iodo substituent.

In carry out this reaction, the compound of formula XV is treated with a halogenating agent, such as a halogen in a solvent, such as iodine dissolved in dimethylformamide, or a halosuccinimide in a conventional solvent medium. Any of the conditions conventionally utilized in halogenating with these halogenating agents can be utilized to carry out this reaction and produce a halo substituent at the 3-position on the indole ring. These halogen aiding agents will selectively halogenate the 3-position on the indole ring without affecting the other positions. The reaction whereby halogenating agents such as iodine are used to halogenate the compound of formula XV, can be carried out utilizing the same procedure as disclosed by Sakamoto et al. in *Chem. Pharm. Bul.*, 1988, 36, pgs. 2248-2252. In addition, any of the conventional well known procedures for providing other leaving groups such as mesyloxy or tosyloxy can be utilized to produce a leaving group at the 3-position of the indole ring on the compound of formula XV.

EXAMPLES

The following examples are provided to illustrate, but not limit, the invention. Although the forgoing invention has been described in some detail by way of illustration and example for purposes of clarity and understanding, it will be apparent to those skilled in the art that certain changes and modification may be practical. Therefore, the description and examples should not be construed as limiting the scope of the invention, which is delineated by the appended claims. Further, the methods for the synthesis of single compounds are directly amenable to the synthesis of small molecule compound libraries using split-and-pool techniques, which are known in the art.

General Methods

Reagents were purchased from Aldrich, Sigma, Bachem Biosciences, Advanced ChemTech, Lancaster and Argonaut Argogel and used without further purification. Washing resins, either free flowing or in devices, for effecting solvent permeable resin segregation appropriate for split and mix combinatorial synthesis involves the addition of a stated solvent and agitation of the solid phase in that solvent for at least 3 minutes before the solvent is then filtered away from the solid phase polymer. This constitutes washing one time; solid phase polymers are routine washed several times in a series of solvents. After cleavage of organic products from the solid phase, concentration of solutions was performed by reduced pressure rotary evaporation, or using the Savant SpeedVac and Genevac rotary evaporator instruments. NMR (nuclear magnetic resonance) spectra were recorded on a Bruker 300 Mhz instrument with CDCl$_3$ as solvent unless noted. $^1$H NMR data are reported as follows: chemical shifts relative to tetramethylsilane (0.00 ppm), multiplicity (s=singlet, d=doublet, dd=doublet of doublets, t=triplet, m=multiplet), coupling, and integration. Assignment of protons was aided by decoupling experiments. LC/MS (liquid chromatography mass spectroscopy) spectra were recorded using the following system. For measurement of mass spectra the system was configured with a Micromass Platform II: API Ionization in positive electrospray (mass range: 150-1200 amu). The simultaneous chromatographic separation was achieved with the following HPLC system: Column, ES Industries Chromegabond WR C-18 3u 120 Å (3.2×30 mm) Cartridge; Mobile Phase A: Water (0.02% TFA) and Phase B: Acetonitrile (0.02% TFA); gradient 10% B to 90% B in 3 minutes; equilibration time, 1 minute; flow rate of 2 ml/minute.

The following abbreviations are used in the description of experimental procedures: eq for equivalent; DMF for dimethyl-formamide, NaHCO$_3$ for sodium bicarbonate, HATU for 0-(7-azabenzotriazol-1-yl)-1,1,3,3-tetramethyluronium hexafluorophosphate, HBTU for O-(benzotriazol-1-yl)-1,1,3,3-tetramethyluronium hexafluorophosphate, DIPEA for diisopropyl-ethylamine, DME for dimethylethyleneglycol, CH$_3$CN for acetonitrile, DCM or CH$_2$Cl$_2$ for dichloromethane, CH$_3$OH for methyl alcohol, ClCH$_2$CH$_2$Cl for dichloroethane, TFA for trifluoroacetic acid, Boc for bis-ter-butyloxycarbonyl, DME for dimethoxyethane, and FMPB for formylmethoxyphenoxybutyric acid amide derivatived polystyrene.

The Wang Resin used was Wang Resin HL which is a hydroxymethylphenoxy bonded to a polystyrene matrix such as disclosed by Wang et al. (1976) *J. Org. Chem.* 41:3258; Rich et al. (1975) *J. Am. Chem. Soc.* 97:1575-1579.

General procedure for synthesis of 3-iodo-1H-indole-2-carboxylic acid:

1.0 mmol of 1H-Indole-2-carboxylic acid and 3.8 mmol of KOH were dissolved in 7 ml of water. 1 mmol of I$_2$ was dissolved in 1.1 ml of DMF. The I$_2$ solution was added to the aqueous solution drop wise. The result solution was stirred for another 30 minutes. The reaction was monitored by HPLC. The solution was acidified by 1N hydrochloric acid to pH 4 to 5. 3-iodo-1H-indole-2-carboxylic acid was filtered and washed by more water.

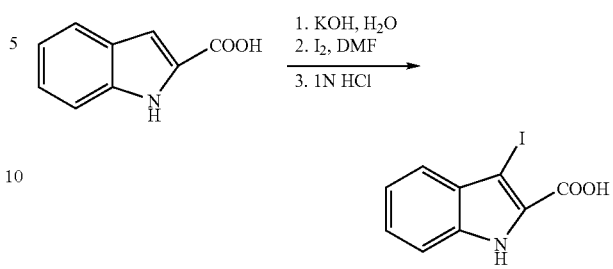

Alternative procedure for synthesis of 3-iodo-1H-indole-2-carboxylic acid:

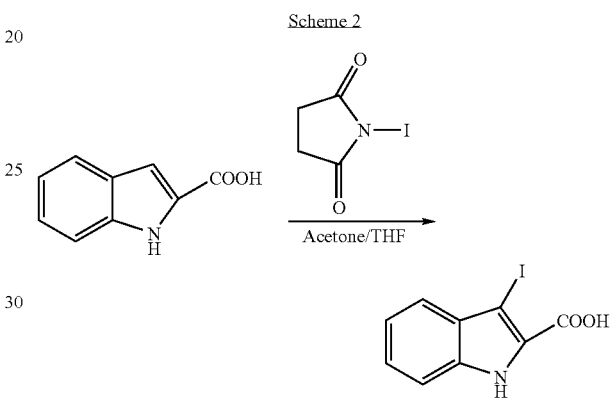

This procedure was carried out as disclosed by Sakamoto et al. (Sakamoto, T.; Nagano, T.; Kondo, Y.; Yamanaka, H. *Chem. Pharm. Bull.*, 1988, 36, 2248-2252). 1.0 mmol of 1H-Indole-2-carboxylic acid was dissolved in 10 ml of acetone. 1.0 mmol of N-iodosuccinimide (NIS) was dissolved in 2 ml of acetone. The NIS solution was added to the solution of 1H-Indole-2-carboxylic acid dropwise. The reaction solution was stirred for another hour. At this time, the reaction mixture was concentrated under reduced pressure. The resulting solid was washed by water three times and filtered. The final product was dried under the vacuum.

Method A: General Procedures for Solid Phase Preparations of 3-aryl-1H-indole-2-carboxylic acids.

a) Load of 3-iodo-1H-indole-2-carboxylic acid to Wang Resin: To a suspension of 100 Resin segregation devices, each containing Wang Resin HL (IRORI Unisphere 200, 88 µmol equivalent/Resin segregation device, 8.8 mmol in total) in 120 ml of DMF were added 3-iodo-1H-indole-2-carboxylic acid (44 mmol), HATU (16.72 g, 44 mmol), and di-isopropyl ethyl amine (44 mmol). The suspension was shaken overnight at room temperature under an atmosphere of argon. The solvent was filtered and the Resin segregation devices were washed with DMF four times, with methanol four times, methylene chloride four times and hexanes four times. The Resin segregation devices were dried under the vacuum over night at room temperature.

b) BOC protection: The Resin segregation devices were suspended in 120 ml of DMF and BOC anhydride (50.5 ml, 0.22 mol), DMAP (5.38 g, 44 mmol), and triethylamine (62 ml, 0.44 mol). The suspension was shaken overnight under an atmosphere of argon. The solvent was filtered and the Resin segregation devices were washed with DMF four times, with methanol four times, methylene chloride four times and hexanes four times. The Resin segregation devices were dried under the vacuum over night at room temperature.

c) Aryl coupling: To 10 resin segregation devices (0.88 mmol total equivalence) in 10 ml of DME was added tetrakis (triphenylphosphine)palladium(0) (0.15 g, 0.132 mmol) and shaken for 15 minutes. Phenyl boronic acid (4.4 mmol) and 2M (aqueous) Na$_2$CO$_3$ (2 ml, 4.9 mmol) were added to the solution. The suspension was heated at 90° C. for 14 hours under an argon atmosphere. The solvent was filtered off and the Resin segregation devices were washed with DMF four times, with methanol four times, methylene chloride four times and hexanes four times. The Resin segregation devices were dried under the vacuum over night at room temperature.

d) Cleavage: The Resin segregation devices were sorted into single cleavage wells and treated with taken into the cleavage using TFA in DCM (vol/vol 1:1) at room temperature for 2 hours. The solution was drained into tared, bar coded vials and the resin was rinsed with one 1 mL DCM. The solvents were removed under reduced pressure on a Savant SpeedVac or Genevac rotary evaporator instruments providing the crude 3-phenyl-1H-indole-2-carboxylic acid.

The compound shown in Example is a typical compound obtained via Method A.

Example 1

5-chloro-3-phenyl-1H-indole-2-carboxylic acid

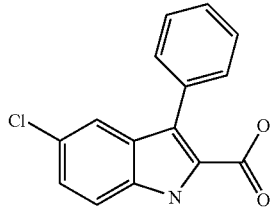

$^1$H-NMR (DMSO-D$_6$): 12.05 (s, 1H), 7.60-7.20 (m, 8H). LCMS(10-90% acetonitrile-water): C$_{15}$H$_{10}$ClNO$_2$=271, 271.11, 2.05 min, 100%.

General Procedures for Solid Phase Preparations of 3-aryl-1H-indole-2-carboxylic acids.

a) Load of 3-iodo-1H-indole-2-carboxylic acid to Wang Resin (hydroxymethylphenoxy bounded to polystyrene matrix): To a suspension of 100 Resin segregation devices, each containing Wang Resin HL (IRORI Unisphere 200, 88 μmol equivalent/Resin segregation device, 8.8 mmol in total) in 120 ml of DMF were added 3-iodo-1H-indole-2-carboxylic acid (44 mmol), HATU (16.72 g, 44 mmol), and di-isopropyl ethyl amine (44 mmol). The suspension was shaken overnight at room temperature under an atmosphere of argon. The solvent was filtered and the Resin segregation devices were washed with DMF four times, with methanol four times, methylene chloride four times and hexanes four times. The Resin segregation devices were dried under the vacuum over night at room temperature.

b) BOC protection: The Resin segregation devices were suspended in 120 ml of DMF and BOC anhydride (50.5 ml, 0.22 mol), DMAP (5.38 g, 44 mmol) and triethylamine (62 ml, 0.44 mol). The suspension was shaken overnight under an atmosphere of argon. The solvent was filtered and the Resin segregation devices were washed with DMF four times, with methanol four times, methylene chloride four times and hexanes four times. The Resin segregation devices were dried under the vacuum over night at room temperature.

c) Aryl coupling: To 10 resin segregation devices (0.88 mmol total equivalence) in 10 ml of DME was added tetrakis (triphenylphosphine)palladium(0) (0.15 g, 0.132 mmol) and shaken for 15 minutes. Phenyl boronic acid (4.4 mmol) and 2M (aqueous) Na$_2$CO$_3$ (2 ml, 4.9 mmol) were added to the solution. The suspension was heated at 90° C. for 14 hours under an argon atmosphere. The solvent were filtered off and the Resin segregation devices were washed with DMF four times, with methanol four times, methylene chloride four times and hexanes four times. The Resin segregation devices were dried under the vacuum over night at room temperature.

d) Cleavage: The Resin segregation devices were sorted into single cleavage wells and taken into the cleavage using TFA in DCM (vol/vol 1:1) at room temperature for 2 hours. The solution was drained into tared, bar coded vials and the resin was rinsed with one 1 mL DCM. The solvents were removed under reduced pressure on a Savant SpeedVac or Genevac rotary evaporator instruments providing the crude 3-phenyl-1H-indole-2-carboxylic acid.

Example 2

Benzyl-5-Chloro-3-(4-methylphenyl)indole-2-carboxylic acid

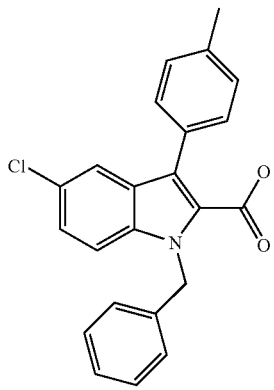

$^1$H-NMR (DMSO-D$_6$): 7.61(d, J=9.2 Hz, 1H), 7.20-7.03 (m, 12H), 6.98 (d, J=7.6 Hz, 2H), 5.77(s, 2H), 2.35(s, 3H). LCMS(10-90% acetonitrile): C$_{23}$H$_{18}$ClNO$_2$=375, 375.22, 2.86 min, 100%.

General Procedures for Solid Phase Preparations of 1-substituted-3-aryl-1H-indole-2-carboxylic acid.

a) Load of 3-iodo-1H-indole-2-carboxylic acid to Wang Resin (hydroxymethylphenoxy bounded to polystyrene matrix): To a suspension of 100 Resin segregation devices each containing Wang Resin HL (IRORI Unisphere 200, 88 μmol equivalent/Resin segregation device, 8.8 mmol in total) in 120 ml of DMF were added 3-iodo-1H-indole-2-carboxylic acid (44 mmol), HATU (16.72 g, 44 mmol) and di-isopropyl ethyl amine (44 mmol). The suspension was shaken overnight at room temperature under an atmosphere of argon. The solvent was filtered and the Resin segregation devices were washed with DMF four times, with methanol four times, methylene chloride four times and hexanes four times. The Resin segregation devices were dried under the vacuum over night at room temperature.

b) N¹-alkylation: To a suspension of 500 resin segregation devices (88 μmol equivalent/Resin segregation device, 44 mmol total for 500 resin segregation devices) in 500 ml of DMF was added NaH (60% dispersion in mineral oil, 14.0 g, 0.35 mol), The suspension was shaken 30 min at RT. At that time, benzyl bromide (4.50 g, 0.26 mmol) was added. The reaction mixture was shaken overnight under an atmosphere of argon. The solvent was filtered and the Resin segregation devices were washed with DMF four times, with methanol four times, methylene chloride four times and hexanes four times. The Resin segregation devices were dried under the vacuum over night at room temperature and sorted c) Aryl coupling:. To 10 resin segregation devices (0.88 mmol total equivalence) in 10 ml of DME was added tetrakis (triphenylphosphine)palladium(0) (0.15 g, 0.132 mmol) and shaken for 15 minutes. Phenyl boronic acid (4.4 mmol) and 2M (aqueous) Na₂CO₃ (2 ml, 4.9 mmol) were added to the solution. The suspension was heated at 90° C. for 14 hours under an argon atmosphere. The solvent were filtered off and the Resin segregation devices were washed with DMF four times, with methanol four times, methylene chloride four times and hexanes four times. The Resin segregation devices were dried under the vacuum over night at room temperature.

d) Cleavage: The Resin segregation devices were sorted into single cleavage wells and treated with taken into the cleavage using TFA in DCM (vol/vol 1:1) at room temperature for 2 hours. The solution was drained into tared, bar coded vials and the resin was rinsed with one 1 mL DCM. The solvents were removed under reduced pressure on a Savant SpeedVac or Genevac rotary evaporator instruments providing the crude 3-phenyl-1H-indole-2-carboxylic acid.

The invention claimed is:

1. The compound with the structure:

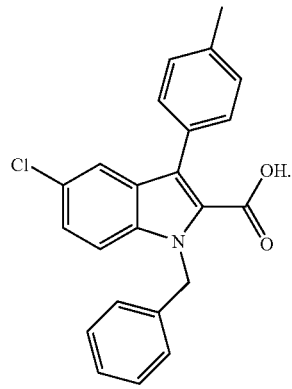

* * * * *